US010220121B2

(12) United States Patent
Bharat

(10) Patent No.: US 10,220,121 B2
(45) Date of Patent: Mar. 5, 2019

(54) CHEST TUBE DRAINAGE SYSTEM WITH ANALYZER

(71) Applicant: Northwestern University, Evanston, IL (US)

(72) Inventor: Ankit Bharat, Chicago, IL (US)

(73) Assignee: Northwestern University, Evanston, IL (US)

( * ) Notice: Subject to any disclaimer, the term of this patent is extended or adjusted under 35 U.S.C. 154(b) by 169 days.

(21) Appl. No.: 15/404,555

(22) Filed: Jan. 12, 2017

(65) Prior Publication Data

US 2017/0119938 A1    May 4, 2017

Related U.S. Application Data

(62) Division of application No. 14/577,880, filed on Dec. 19, 2014, now Pat. No. 9,545,462.

(Continued)

(51) Int. Cl.
*A61M 1/00* (2006.01)
*A61M 16/10* (2006.01)
(Continued)

(52) U.S. Cl.
CPC ........ *A61M 1/0025* (2014.02); *A61M 1/0013* (2013.01); *A61M 1/0035* (2014.02);
(Continued)

(58) Field of Classification Search
CPC .............. A61M 1/0013; A61M 1/0025; A61M 1/0035; A61M 1/0086; A61M 16/10;
(Continued)

(56) References Cited

U.S. PATENT DOCUMENTS 3,683,913 A    8/1972    Kurtz et al.
4,592,741 A    6/1986    Vincent
(Continued)

FOREIGN PATENT DOCUMENTS

WO    WO 09/135070    11/2009
WO    WO 11/112291     9/2011
WO    WO 13/123338     8/2013

OTHER PUBLICATIONS

Oparka et al., The Application of Capnouaphy to Differentiate Peri-Chest Tube Air Leak From Parenchymal Leak Following Pulmonary Surgery, Annals of Cardiothoracic Surgery, (3)2:219-220 (Mar. 2014) (2 pages).

(Continued)

*Primary Examiner* — Adam Marcetich
(74) *Attorney, Agent, or Firm* — Cook Alex Ltd.

(57) ABSTRACT

A system includes a chest tube drainage system comprising a first chamber in fluid communication with a port connectable to a chest tube, a second chamber in fluid communication with a port connectable to a suction device, and a fluid seal connected to and disposed between the first chamber and the second chamber. The system also includes one or more gas sensors attached to the chest tube drainage system, the one or more gas sensors configured to detect at least one of gaseous carbon dioxide and gaseous oxygen, a controller connected to the one or more gas sensors, and at least one indicator coupled to the controller. The controller is configured to determine if a threshold level of carbon dioxide is exceeded, and to activate the at least one indicator if the threshold level of carbon dioxide is not exceeded.

8 Claims, 6 Drawing Sheets

Related U.S. Application Data

(60) Provisional application No. 61/918,913, filed on Dec. 20, 2013.

(51) Int. Cl.
*A61M 39/28* (2006.01)
*A61B 5/00* (2006.01)
*A61B 5/08* (2006.01)

(52) U.S. Cl.
CPC ......... *A61M 1/0086* (2014.02); *A61M 16/10* (2013.01); *A61M 39/28* (2013.01); *A61B 5/08* (2013.01); *A61B 5/7275* (2013.01); *A61M 16/1005* (2014.02); *A61M 2202/0208* (2013.01); *A61M 2202/0225* (2013.01); *A61M 2205/3303* (2013.01); *A61M 2205/3344* (2013.01); *A61M 2205/587* (2013.01); *A61M 2210/101* (2013.01); *A61M 2210/1025* (2013.01); *A61M 2210/1039* (2013.01); *A61M 2230/005* (2013.01); *A61M 2230/432* (2013.01); *A61M 2230/435* (2013.01)

(58) Field of Classification Search
CPC ...... A61M 16/1005; A61M 2202/0208; A61M 2202/0225; A61M 2205/3303; A61M 2205/3344; A61M 2205/587; A61M 2210/101; A61M 2210/1025; A61M 2210/1039; A61M 2230/005; A61M 2230/432; A61B 5/08; A61B 5/7275
See application file for complete search history.

(56) References Cited

U.S. PATENT DOCUMENTS

| | | | |
|---|---|---|---|
| 4,654,029 A * | 3/1987 | D'Antonio | A61M 1/0031 600/584 |
| RE35,225 E | 4/1996 | Herweck et al. | |
| 5,738,656 A | 4/1998 | Wagner | |
| 7,575,553 B2 | 8/2009 | Stahmann et al. | |
| 2003/0212337 A1 | 11/2003 | Sirokman | |
| 2004/0260255 A1* | 12/2004 | Charlez | A61M 1/0013 604/317 |
| 2005/0203469 A1 | 9/2005 | Bobroff et al. | |
| 2005/0240093 A1* | 10/2005 | DeArmond | A61B 5/02042 600/372 |
| 2006/0025650 A1 | 2/2006 | Gavriely | |
| 2008/0072905 A1* | 3/2008 | Baker | A61B 5/0836 128/204.23 |
| 2009/0118646 A1 | 5/2009 | Svanberg et al. | |
| 2009/0264833 A1 | 10/2009 | Boyle, Jr. | |
| 2010/0078018 A1 | 4/2010 | Heinonen et al. | |
| 2010/0130947 A1 | 5/2010 | Daly | |
| 2010/0170507 A1* | 7/2010 | Tanaka | A61M 16/0429 128/202.22 |
| 2010/0174270 A1 | 7/2010 | Charlez et al. | |
| 2011/0017218 A1* | 1/2011 | Davies | A61M 1/04 128/207.16 |
| 2011/0040286 A1 | 2/2011 | Boyle, Jr. et al. | |
| 2011/0071415 A1 | 3/2011 | Karwoski et al. | |
| 2011/0201956 A1 | 8/2011 | Alferness et al. | |
| 2013/0110057 A1 | 5/2013 | Croteau et al. | |
| 2013/0312754 A1 | 11/2013 | Garde et al. | |
| 2014/0100540 A1 | 4/2014 | Linder et al. | |
| 2014/0163489 A1 | 6/2014 | Walti et al. | |
| 2014/0323906 A1* | 10/2014 | Peatfield | A61B 5/036 600/561 |
| 2015/0031968 A1 | 1/2015 | Miserlis et al. | |

OTHER PUBLICATIONS

International Search Report and Written Opinion, counterpart International Appl. No. PCT/US2014/071655, dated Oct. 4, 2015 (14 pages).

* cited by examiner

CHEST TUBE DRAINAGE SYSTEM WITH ANALYZER

BACKGROUND

This patent is directed to an apparatus and method for determining when a chest tube should be removed, and in particular to an apparatus and method for determining when a chest tube should be removed combinable with a chest tube drainage system.

Each year, over 380,000 lung resections and other events require a chest tube that drains air, and potentially fluids, leaking from the cut surface of the lung into the pleural space. All patients following chest surgery will have at least one chest tube, with some patients having more than one chest tube. The chest tube is attached to a drainage system in which the fluids exiting the chest tube are collected in a collection chamber. The drainage system is in turn attached to suction, to draw fluids and gases out of the pleural space into the drainage system.

At some point, the chest tube should be removed. The chest tube exits between the rib spaces and may impinge the intercostal nerves. This causes discomfort and requires intravenous pain medications. However, if the chest tube is removed too early, the removal of the chest tube can lead to lung collapse and cause major complications.

Air leaks are the largest determinant for leaving chest tubes in patients following cardiothoracic lung procedures. Typically, the decision to remove the chest tube is based on a crude visual inspection (VI) of the drainage system to determine if there is a leak into the plural space. If the visual inspection suggests that a leak exists, then the chest tube is left in place.

While a visual inspection may very well lead to the detection of a leak originating from the cut surface of the lung, the "detected" leak may also be the result of residual intrapleural air, a leak into the pleural space from the outside (e.g., through the chest tube incision around the chest tube), or reverse airflow in the chest tube. It is typically unclear from a simple visual inspection what the source of the "leak" might be. Further, the visual inspection technique may be influenced by patient effort, tube position and presence of fluid or clots in the chest tube, for example.

As mentioned above, if the chest tube is removed based on a visual inspection that is incorrect (e.g., the inspection suggests that there is no leak, or a detected leak is attributed to a cause other than the cut surface of the lung), the removal of the chest tube could lead to lung collapse, requiring replacement of the chest tube. Replacement of the chest tube could lead to complications. In any event, lung collapse and chest tube replacement will increase the length of the hospital stay.

Considering the potential downside of a premature determination of the absence of a leak, healthcare professionals may elect to leave the chest tube in even though there is no actual leak (e.g., the detected leak is attributable to the presence of residual intrapleural air). Of course, this also will increase the length of hospital stay, and leaving the chest tube in when not indicated could also lead to complications.

The costs of a prolonged hospital stay are considerable. Each additional day that a patient spends hospitalized on the thoracic surgery floor is approximately 6500 dollars, although that amount can vary. Moreover, prolonged hospitalization can lead to complications from deep vein thrombosis, pneumonia, hospital acquired infections, etc.

As set forth in more detail below, the present disclosure sets forth a method and an analyzer for use with a chest tube drainage system, as well as the entire system so defined, embodying advantageous alternatives to the existing visual inspection methods.

SUMMARY

According to one aspect of the present disclosure, a system includes a chest tube drainage system comprising a first chamber in fluid communication with a port connectable to a chest tube, a second chamber in fluid communication with a port connectable to a suction device, and a fluid seal connected to and disposed between the first chamber and the second chamber. The system also includes one or more gas sensors disposed at the port connectable to the suction device or between the port and the fluid seal, the one or more gas sensors configured to detect at least one of gaseous carbon dioxide and gaseous oxygen. According to further aspects, the gas sensors may detect gaseous carbon dioxide and oxygen, and the system may include at least one pressure sensor as well.

According to another aspect of the present disclosure, a system includes a chest tube drainage system comprising a first chamber in fluid communication with a port connectable to a chest tube, a second chamber in fluid communication with a port connectable to a suction device, and a fluid seal connected to and disposed between the first chamber and the second chamber. The system also includes one or more gas sensors attached to the chest tube drainage system, the one or more gas sensors configured to detect at least one of gaseous carbon dioxide and gaseous oxygen, a controller connected to the one or more gas sensors, and at least one indicator coupled to the controller. The controller is configured to determine if a threshold level of carbon dioxide is exceeded, and to activate the at least one indicator if the threshold level of carbon dioxide is not exceeded. According to further aspects, the gas sensors may detect gaseous carbon dioxide and oxygen, and the system may include at least one pressure sensor as well.

According to a further aspect of the present disclosure, a method of determining if a chest tube is to be removed includes the steps of determining if a threshold level of carbon dioxide is exceeded in a chest tube drainage system connected to a chest tube downstream of a liquid seal, and removing the chest tube if the threshold level of carbon dioxide is not exceeded. According to further aspects, the method may include determinations based on threshold levels of oxygen and pressure as well.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION OF VARIOUS EMBODIMENTS

Figure 1:
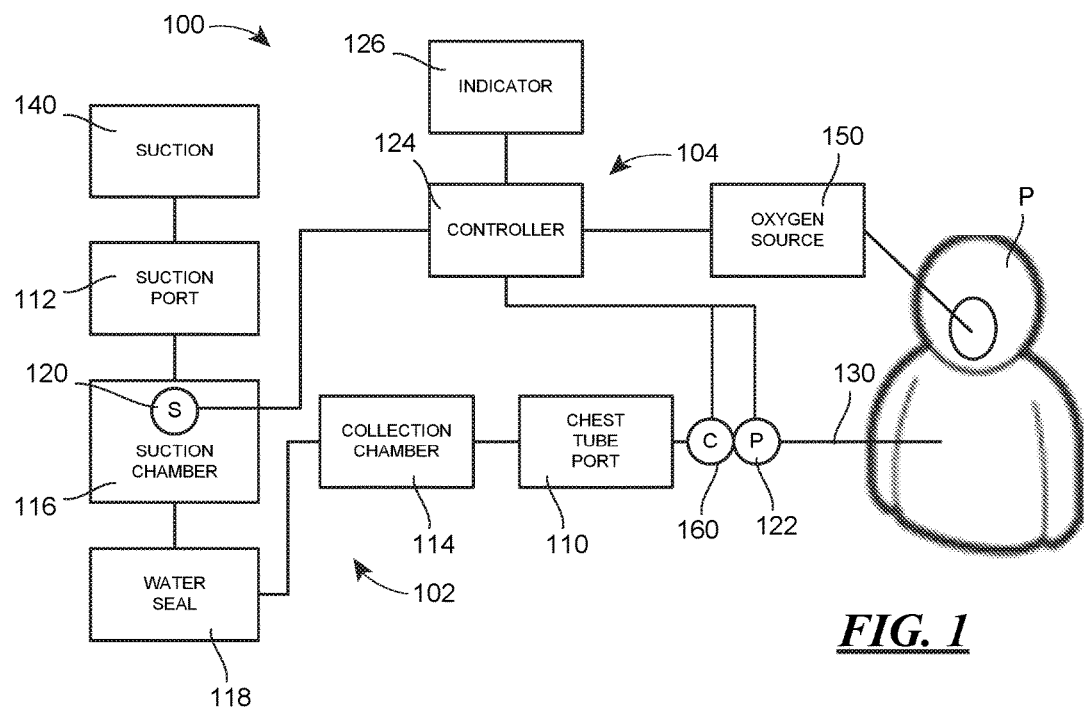
FIG. 1 is a schematic view of a system including an analyzer according to an embodiment of the present disclosure.

FIG. 1 is an illustration of the system 100 including a chest tube drainage system 102 and an analyzer 104 for use with a patient P. The chest tube drainage system 102 includes ports 110, 112, chambers 114, 116, and a fluid seal 118. The analyzer 104 includes one or more gas sensors 120, a pressure sensor 122, a controller 124, and an indicator 126. The system 100 may also include a chest tube 130, a suction device 140, and a supplemental oxygen source 150.

The analyzer 104 utilizes the gas sensors 120, and optionally the pressure sensor 122, to determine whether the chest tube 130 may be removed. In particular, the determination whether the chest tube 130 may be removed is performed by the controller 124. If the determination is made that the chest tube 130 may be removed, the controller activates the indicator 126 to signal the doctor or other healthcare professional using the analyzer 104 that the tube 130 may be removed. Non-activation of the indicator 126 or activation of a different indicator 126 may signal the doctor or other healthcare professional that the chest tube 130 may not be removed. In either event, activation of the indicator 126 may provide a positive signal to the doctor or healthcare professional (e.g., a light is turned on) or a negative signal (e.g., a light that is initially on is turned off).

Returning to FIG. 1, it will be recognized that the chest tube drainage system 102 has a chest tube port 110 that is connectable to the chest tube 130. As illustrated, the chest tube port 110 is connected to the chest tube 130 with a clamp 160 disposed between the port 110 and the chest tube 130, and the pressure sensor 122 disposed between the clamp 160 and the chest tube 130. The first chamber 114 is in fluid communication with the chest tube port 110. Used in this sense, fluid communication may include a connection that permits both gaseous and liquid forms of fluids to pass therethrough.

The first chamber 114, which may be referred to as the collection chamber, is configured to receive and separate a fluid component from a gaseous component received by the drainage system 102 from the chest tube 130. The fluid seal 118 provides a one-way barrier through which the gaseous component may pass. The fluid seal 118, which may also be referred to as a water seal, is connected to and disposed between the collection chamber 114 and the second chamber 116.

The second chamber 116, which may be referred to as the suction chamber, is in fluid communication with the port 112. The port 112 is, in turn, connectable to the section generator 140. Disposed within the suction chamber 116 are the one or more gas sensors 120, which will be referred to as the gas sensor 120 for simplicity although separate sensors may be used for detection and analysis of different gases. The gas sensor 120 may be disposed anywhere within the suction chamber 116, but preferably may be disposed at or near the port 112 to the suction device 140.

The controller 124 is connected to the gas sensor 120, the pressure sensor 122, the indicator 126, and the clamp 160. According to certain embodiments of the present disclosure, the controller 124 may also be connected to the supplemental oxygen source 150. The controller 124 may be configured to determine if a threshold level of carbon dioxide is exceeded in the suction chamber 116, and to activate the least one indicator 126 if the threshold level of carbon dioxide is not exceeded. As explained previously, activation of the least one indicator 126 would be used to signal the doctor or other healthcare professional that the chest tube 130 may be removed.

The controller 124 may also be configured to determine if a threshold level of oxygen is exceeded in those situations where the threshold level of carbon dioxide is exceeded. The oxygen measured by the gas sensor 120 may be a consequence of the administration of supplemental oxygen from the supplemental oxygen source 150. In this regard, it will also be recognized that while the oxygen source 150 is referred to as the supplemental oxygen source, the oxygen source 150 may also be a primary oxygen source as well. If the controller 124 determines that a threshold level of oxygen is not exceeded, then the controller 124 activates the least one indicator 126 to signal that the chest tube 130 may be removed.

The controller 124 may be further configured to determine if a threshold pressure is exceeded at the pressure sensor 122 if the threshold level of oxygen exceeded. In particular, the controller 124 may be configured to activate the clamp 160, thereby isolating the pressure sensor 122 from the remainder of the drainage system 102. The controller 124 may then use the pressure sensor 122 to determine if the threshold pressure is exceeded. If the threshold pressure is not exceeded, the controller 124 may activate the least one indicator 126 to signal that the chest tube 130 may be removed.

Having thus described the entire system 100, as well as its general operation, the specifics of the system 100 and the operation of the system 100 may now be discussed in detail.

Figure 2:
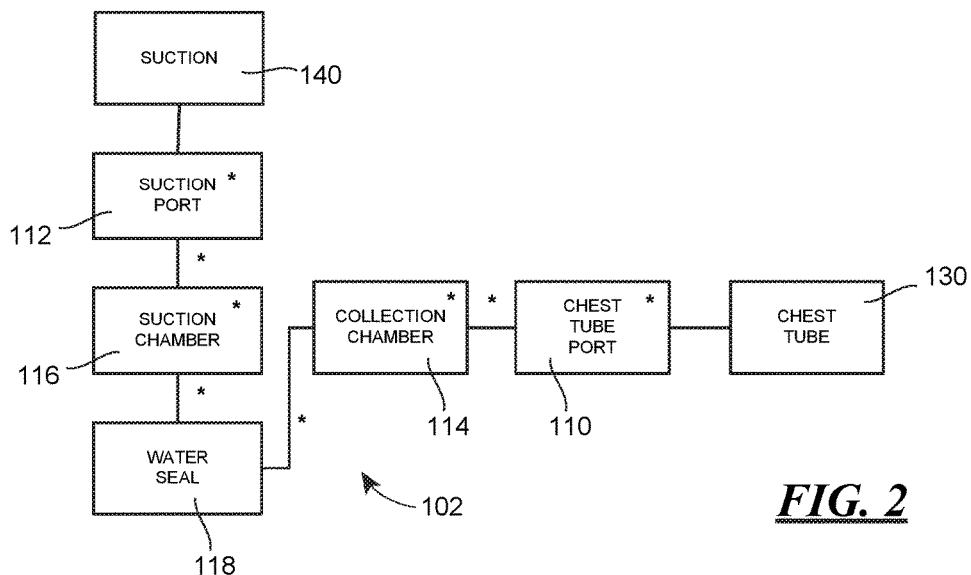
FIG. 2 is a schematic view of a system such as is illustrated in FIG. 1, with locations for the gas and pressure sensors marked.

As illustrated in FIG. 1, the gas sensor 120 is disposed in the suction chamber 116 at or near the suction port 112. As indicated in FIG. 2, the gas sensor 120 may be disposed in a variety of other locations. For example, the gas sensor 120 may be disposed at the chest tube port 110, in the collection chamber 114, at the suction port 112, or at any of the locations connecting the chest tube port 110, the collection chamber 114, the suction chamber 116, the water seal 118, and the suction port 112. Specifically, an asterisk (*) has been placed in FIG. 2 where the gas sensors 120 may be placed.

The gas sensor 120 may be disposed in-line or in parallel to the flow of gases through the drainage system 102. An in-line system would permit the gases to flow past the sensor 120 while the analyzer 104 uses the sensor 120 to analyze the composition of the gases. A parallel circuit arrangement would draw gases to the sensor 120 as the gases flow through the drainage system. A parallel circuit arrangement may be more complicated in that the suction used to draw the gases to the sensor 120 may affect the operation of the drainage system.

It also will be appreciated that placement of the sensor 120 prior to the water seal 118 may have some undesirable consequences. In particular, pleural fluids drawn into the drainage system 102 may come in contact with a gas sensor 120 disposed prior to the water seal 118. This is particularly true where a parallel circuit arrangement is used and the gases must be drawn (with suction) to the sensor 120. The sensor 120 may provide an inaccurate assessment of the gases present at the sensor 120 if the fluid contacts the sensor 120. Therefore, a gas sensor 120 disposed prior to the water seal 118 would need to be shielded from contact with fluids passing into the drainage system 102.

Figure 3:
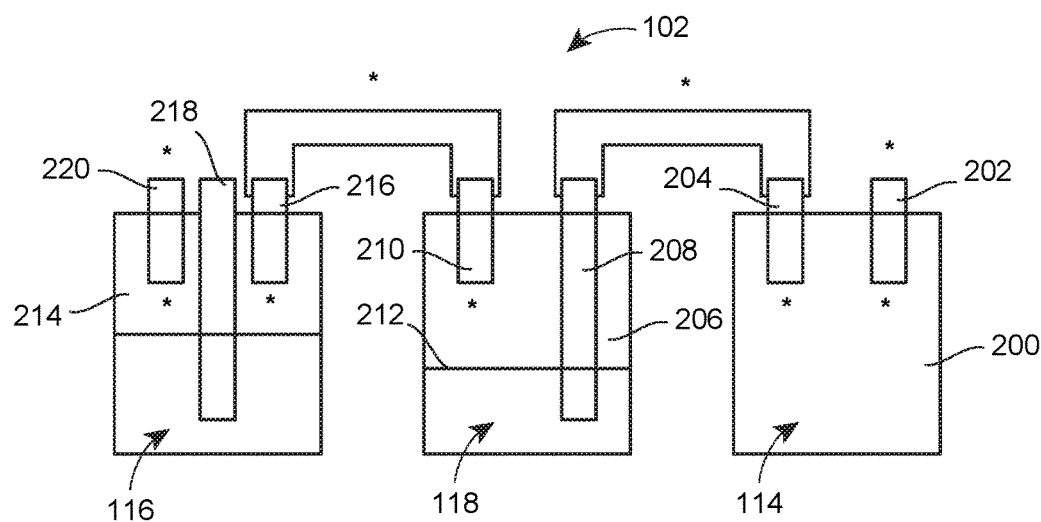
FIG. 3 is a schematic view of a three-chamber drainage system that may be used in the system of FIG. 1.

As illustrated in FIG. 3, the chest tube drainage system 102 may include separate structures that define each of the collection chamber 114, the suction chamber 116, and the water seal 118. The chest tube drainage system 102 illustrated in FIG. 3 may be referred to as a three-bottle system. A first container 200 with cannulas 202, 204 defines the collection chamber 114 and the chest tube port 110 (cannula 202). A second container 206 with cannulas 208, 210 defines the water seal 118. In particular, it will be recognized that the cannula 208 depends further into the container 206 than the cannula 210, and below a water line 212. A third container 214 with cannulas 216, 218, 220 defines the suction chamber 116 and the suction port 112 (cannula 220). It will be recognized that the third container 214 also includes a fluid, and that the cannula 218 depends into the fluid. The depth of the end of the cannula 218 below the surface of the fluid controls the applied suction.

Figure 4:
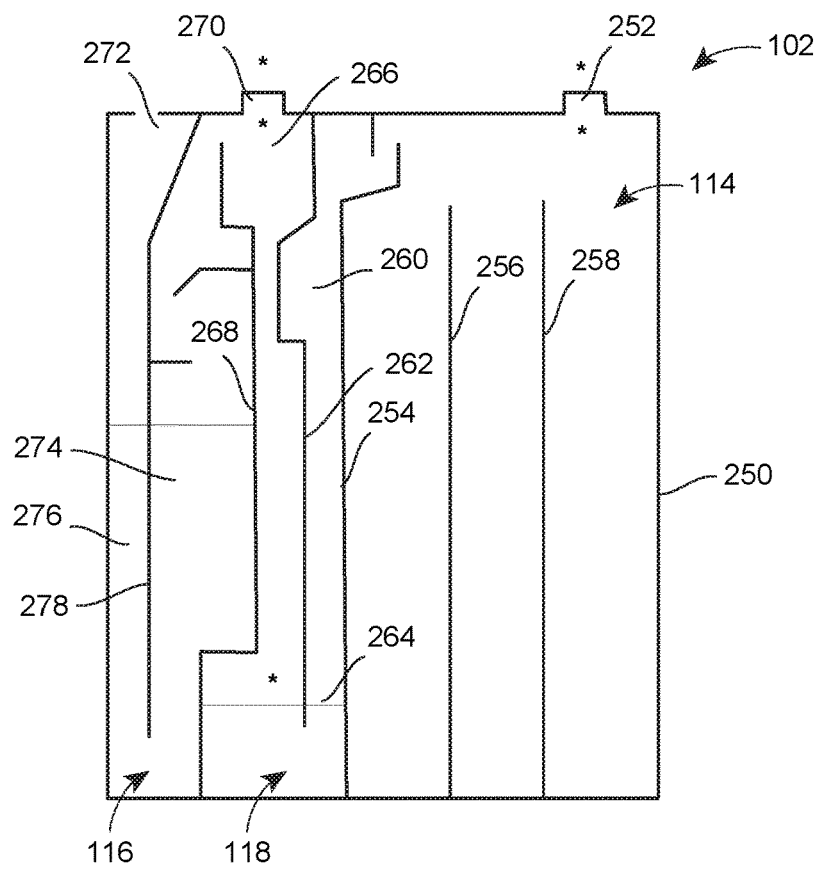
FIG. 4 is a cross-sectional view of a single-housing drainage system that may be used in the system of FIG. 1.

As illustrated in FIG. 4, the chest tube drainage system 102 may also be in the form of a single-housing structure 250, with walls disposed within the single housing 250 defining each of the collection chamber 114, the suction chamber 116, and the water seal 118. Openings in the housing 250 may also define the ports 110, 112.

Specifically, an opening 252 in the housing 250 defines the gas tube port 110. A wall 254 may separate the structures defining the water seal 118 from the structures defining the collection chamber 114. In fact, the collection chamber 114 (which is in fluid communication with the opening 252/port 110) may include one or more walls 256, 258 that subdivide the space that defines the collection chamber 114. A passage 260 is defined by the wall 254 and a second wall 262. The passage 260 ends below a fluid line 264. A second passage 266 is defined by the wall 262 and a second wall 268, and starts below the fluid line 264. The second passage 266 is in fluid communication with an opening 270 that defines the suction port 112. It will also be recognized that the housing 250 may have a further opening 272 that connects with a pair of passages 274, 276 separated by a wall 278, and from the passage 266 by the wall 268. The passages 274, 276 are also partially fluid filled, and function in a fashion similar to that of the cannula 218 in the embodiment of the drainage system 102 illustrated in FIG. 3.

The embodiments of the drainage system 102 illustrated in FIGS. 3 and 4 have been marked, similar to FIG. 2, to show the possible locations for placement of the gas sensors 120 in the drainage system 102. Specifically, an asterisk (*) has been placed in the locations of the embodiments of FIGS. 3 and 4 where the gas sensors 120 may be placed. In addition, the gas sensor 120 may be disposed between the clamp 160 that the patient, P.

It will be recognized that still other embodiments of the drainage system 102 exist, such as may be manufactured by Atrium USA (Hudson, N.H.), Teleflex Medical (Research Triangle Park, N.C.), Covidien (Mansfield, Mass.), and Medela AG (Baar, Switzerland). These embodiments may include a mechanical one-way valve in place of the water seal referred to above, which also may be referred to as a one-way valve, in consideration of the fact that the water seal permits the flow of gases in one direction and resists the flow of gases in the other direction. Furthermore, while the examples of the drainage system 102 illustrated herein are examples of a drainage system using wet suction control, other embodiments of the drainage system 102 may use dry suction control instead.

As to the analyzer 104, and in particular the controller 124, the controller 124 may be defined by individual circuits, or a microprocessor or other programmable device with associated firmware or software. In particular, the controller 124 may be defined by a processor and associated memory, which memory may be used to store instructions that cause the processor to receive information from and/or control the sensors 120, 122 the indicator 126 and the supplemental oxygen source 150.

Figure 5:
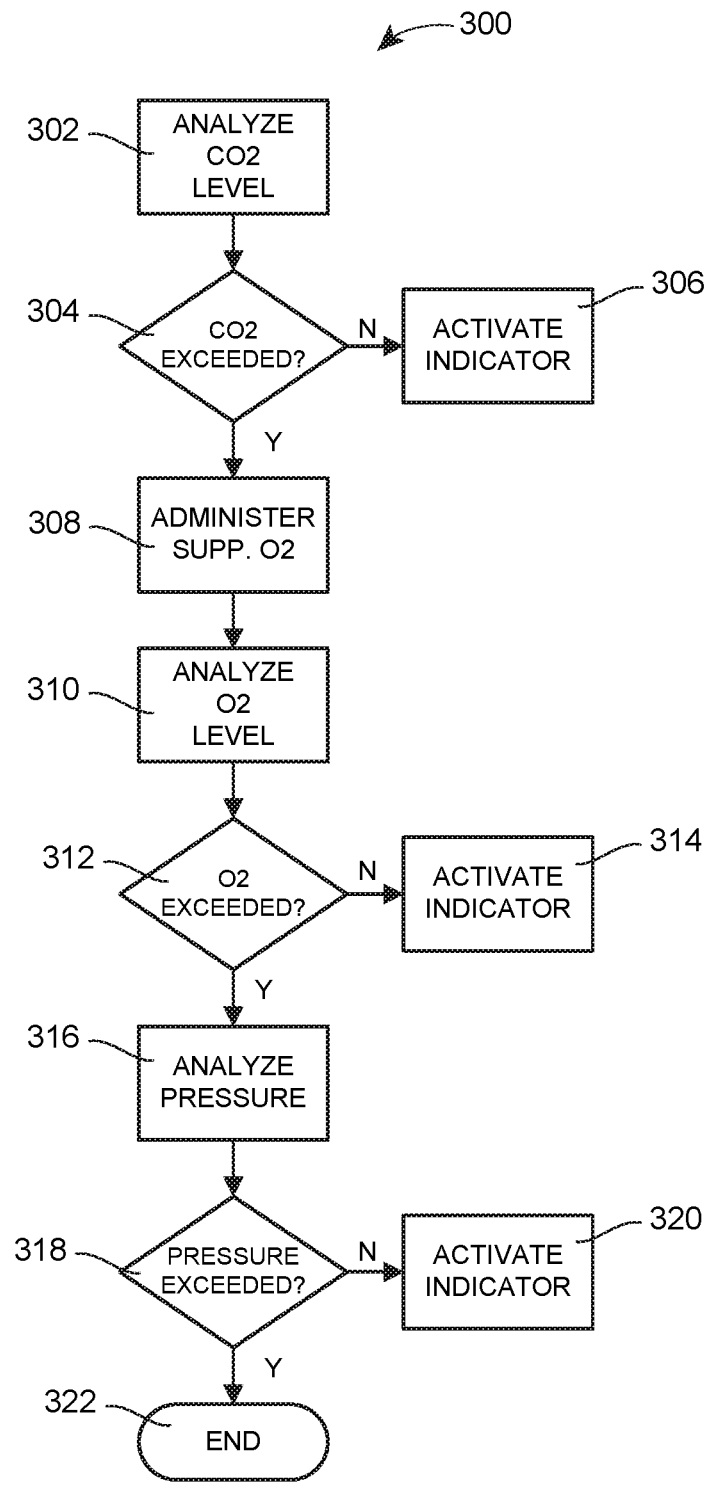
FIG. 5 is a flowchart of a method of operating the analyzer illustrated in FIG. 1.
Figure 6A:
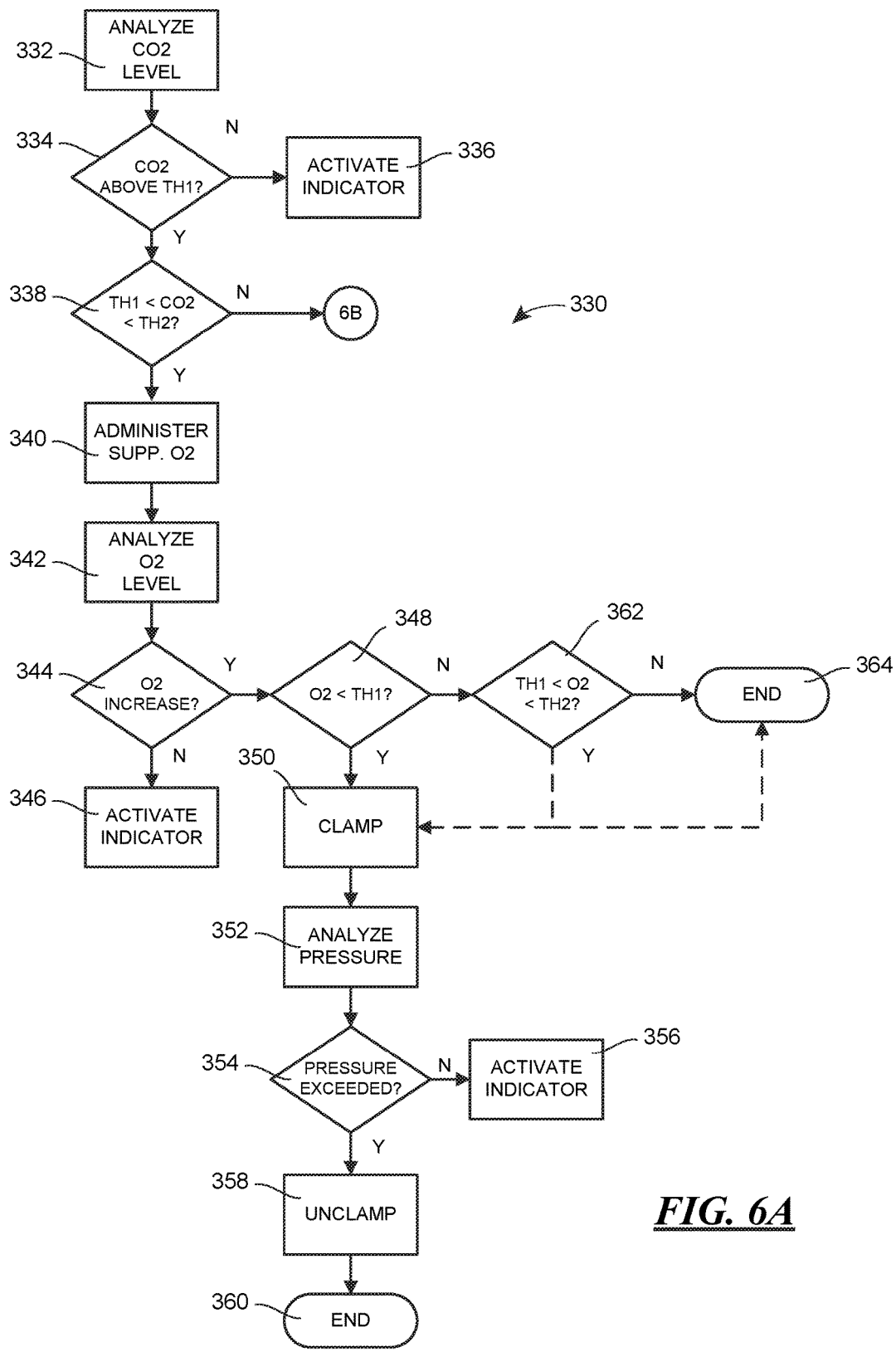
FIGS. 6A and 6B is a flowchart of a detailed method of operating the analyzer illustrated in FIG. 1.

FIGS. 5 and 6A/6B are flow charts of methods of operating the analyzer 104, the controller 124 being configured or programmed to carry out these methods.

Beginning first with the method 300 illustrated in FIG. 5, the method 300 begins at block 302 wherein the controller 124 uses the sensor 120 analyze the level of carbon dioxide at the sensor 120. If the controller 124 determines at block 304 that the level of carbon dioxide at the sensor 120 does not exceed a threshold level, the controller 124 activates the indicator 126 at block 306 to signal to the doctor or other healthcare professional that the chest tube 130 may be removed. If the controller 124 determines at block 304 that the level of carbon dioxide of the sensor 120 exceeds the threshold level, then the method continues to block 308.

At block 308, the controller 124 activates the supplemental oxygen source 150 to administer oxygen to the patient. The controller 124 then uses the sensor 120 to analyze the level of oxygen at the sensor 120 at block 310. If the controller 124 determines at block 312 that the level of oxygen at the sensor 120 does not exceed a threshold level, the controller 124 activates the indicator 126 at the block 314. If the controller 124 determines at block 312 that the level of oxygen at the sensor 120 exceeds a threshold level, then the method may continue at block 316.

At block 316, the controller 124 uses the clamp 160 and the pressure sensor 122 to determine the pressure at the pressure sensor 122. If the controller 124 determines at block 318 that the pressure that the sensor 122 does not exceed a threshold level, the controller 124 activates the indicator 126 at the block 320. If the controller 124 determines at block 318 that the pressure at the sensor 122 exceeds a threshold level, then the method ends at block 322. It will be recognized that the method 300 may be repeated (and will be repeated) during the course of treatment of an individual patient, but even an individual instance of the method 300 is included within the scope of the present disclosure.

Figure 6B:
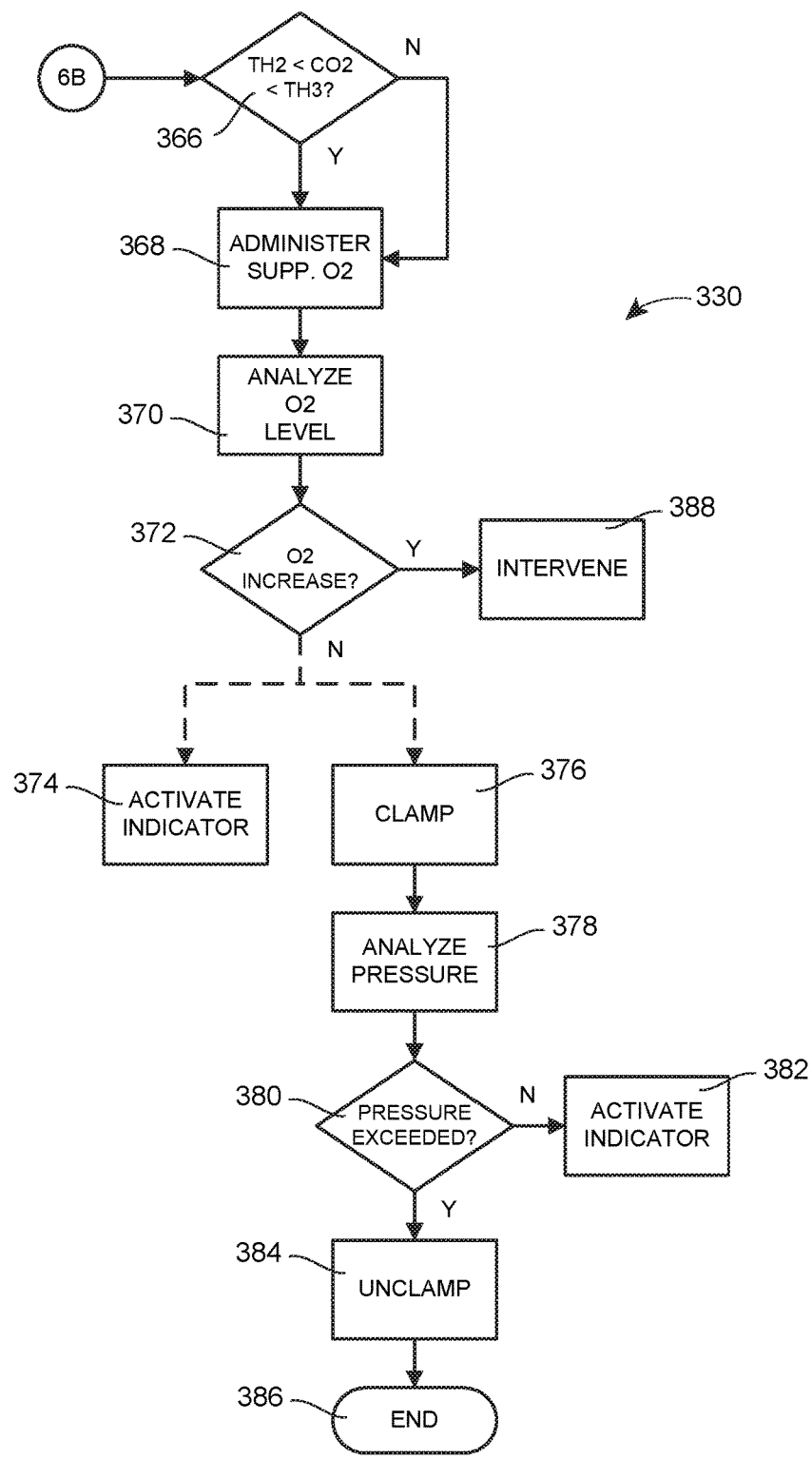

A method 330 similar to the method 300 is illustrated in FIGS. 6A and 6B. The method 330 also utilizes determinations of levels of gaseous carbon dioxide and oxygen, as well as pressure, to determine when to activate the indicator 126, thereby signaling to the doctor or other healthcare professional that the chest tube 130 may be removed. The method 330, however, provides additional details and levels of sophistication relative to the method 300 described with reference to FIG. 5.

The method 330 begins at block 332 wherein the controller 124 uses the sensor 120 to analyze the level of carbon dioxide at the sensor 120. If the level of carbon dioxide at the sensor 120 does not exceed a first threshold level (TH1) at block 334, then the controller 124 activates the indicator 126 at block 336. It is believed at the present time that the first threshold level may be 1% according to certain embodiments. It will be recognized that the threshold level alternatively may be expressed in units of partial pressure of gases (e.g., mmHg or millimeters of mercury); other alternatives are also possible. If the level of carbon dioxide at the sensor 122 exceeds the first threshold level, then the method 330 continues to block 338.

At block 338, the controller 124 makes a further determination whether the level of carbon dioxide at the sensor 120 is between the first threshold level and a second threshold level (TH2). It is believed at the present time that the second threshold level may be 3.5% according to certain embodiments. It will be recognized that the threshold level alternatively may be expressed in units of partial pressure of gases (e.g., mmHg or millimeters of mercury); other alternatives are also possible. If the level of carbon dioxide at the sensor 120 is not between the first and second threshold levels, then the method 300 continues as illustrated in FIG. 6B. If the level of carbon dioxide at the sensor 120 is between the first and second threshold levels, then the method 300 continues at block 340.

At block 340, the controller 124 controls the supplemental oxygen source 150 to administer supplemental oxygen to the patient. The controller 124 then uses the sensor 120 to analyze the level of gaseous oxygen at the sensor 120 at block 342. The method 330 then continues to block 344, wherein the controller 124 determines if there has been an increase in the level of gaseous oxygen at the sensor 120 (e.g., at least 1% increase). If the controller 124 determines there has been no increase in the level of gaseous oxygen at the sensor 120, the controller 124 activates the indicator 126 at block 346. If the controller 124 determines that there has been an increase in the level of gaseous oxygen at the sensor 120, the controller continues to block 348.

At block 348, the controller 124 determines if the increase in oxygen exceeds a first threshold (TH1). It is believed at the present time that the first threshold level may be 5% according to certain embodiments. It will be recognized that the threshold level alternatively may be expressed in units of partial pressure of gases (e.g., mmHg or millimeters of mercury); other alternatives are also possible. If the controller 124 determines that the increase in oxygen does not exceed the first threshold level, the controller 124 activates the clamp 160 at block 350, and analyzes the pressure at the sensor 122 at block 352. If the controller 124 determines at block 354 that the pressure at the sensor 122 does not exceed a threshold level, then the controller 124 activates the indicator 126 at block 356. If the controller 124 determines that block 354 that the pressure at the sensor 122 exceeds a threshold level, then the clamp 160 is undamped at block 358 and the chest tube 130 is not removed at block 360.

If the controller 124 determines at block 348 that the oxygen increased exceeds the first threshold level, the controller 124 proceeds to block 362 and determines if the oxygen increase is between the first threshold level and a second threshold level (TH2). It is believed at the present time that the second threshold level may be 10% according to certain embodiments. It will be recognized that the threshold level alternatively may be expressed in units of partial pressure of gases (e.g., mmHg or millimeters of mercury); other alternatives are also possible. If the controller 124 determines that the increase in oxygen is between the first and second threshold levels at block 362, the controller 124 may optionally be configured or programmed to either proceed to block 350, or to block 364 where the method 330 ends and the chest tube 130 is not removed.

If the controller determines at block 362 that the oxygen increase is not between the first and second threshold levels, then the controller 124 proceeds to block 364, at which point the method 330 ends in the chest tube 130 is not removed.

Returning now to block 338, the method 330 continues to FIG. 6B and block 366. At block 366, the controller 124 determines if the carbon dioxide level is between the second threshold level and a third threshold level (TH3). It is believed at the present time that the third threshold level may be 6% according to certain embodiments. It will be recognized that the threshold level alternatively may be expressed in units of partial pressure of gases (e.g., mmHg or millimeters of mercury); other alternatives are also possible. If the controller 124 determines a block 366 that the carbon dioxide level is between the second and third threshold levels, then the method 330 proceeds to block 368 and supplemental oxygen is administered via the supplemental oxygen source 150.

The controller 124 then determines the oxygen level at the sensor 120 at block 370. The method 330 then proceeds to block 372, wherein the controller 124 determines if there has been an increase in the level of oxygen at the sensor 120. If the controller 124 determines there has not been an increase in the level of oxygen that the sensor 120, the controller may optionally be programmed either to proceed to block 374 and activate the indicator 126, or to proceed to block 376 and activate the clamp 160. If the controller 124 has been configured or programmed to proceed to block 376, then the controller 124 uses the sensor 122 to determine the pressure at the sensor 122 at block 378. The controller 124 then determines at block 380 if the pressure exceeds a threshold level. If the pressure does not exceed the threshold level, then the method 330 continues to block 382, and the controller 124 activates the indicator 126. If the pressure exceeds a threshold level at block 380, then the controller 124 releases the clamp 160 at block 384, and the method 330 ends at block 386 without the chest tube 130 being removed.

If the controller 124 determines there has been an increase in the level of oxygen at the sensor 120 at block 372, the method 330 may proceed to block 388. At block 388, the controller 124 may control the supplemental oxygen source 150 and the suction 140 to reduce the level of carbon dioxide and increase the level of oxygen. In particular, data suggests that if the gases in the intrapleural space include high levels of carbon dioxide, lung healing may be delayed and local innate immunity suppressed. On the other hand, if supplemental oxygen is administered to displace the carbon dioxide and/or suction is applied to draw carbon dioxide out of the space, lung healing may be expedited, resulting in a decrease in the length of the hospital stay and post-surgical infections. Consequently, in a situation such as may be present at block 388 (high levels of carbon dioxide present, and an oxygen increase suggesting an actual leak in the cut surface of the lung), the controller 124 may intervene to reduce the carbon dioxide levels through the administration of supplemental oxygen and/or increase suction.

In any event, as was the case with method 300, it will be recognized that the method 330 may be repeated (and likely will be repeated) during the course of treatment of an individual patient, but even an individual instance of the method 330 is included within the scope of the present disclosure.

In fact, the particular nature of the intervention may vary according to the specific levels of carbon dioxide and oxygen detected in the intrapleural space. For example, if the carbon dioxide levels are very high (in excess of 6%, for example), supplemental oxygen and suction may be used to reduce the carbon dioxide levels to, for example, 3.5%. Alternatively, if the oxygen levels are particular low, but the carbon dioxide levels are not particular high, supplemental oxygen may be administered to increase the oxygen levels above 15%.

Embodiments according to the present disclosure may provide one or more of the following advantages. The system and method according to embodiments of the present disclosure may reduce the clinical uncertainty as to when to remove the chest tube. As a consequence, the duration of the inpatient hospital stay may be reduced, with a related reduction in the costs of the hospital stay. In addition, the system and method may be integrated with conventional chest drainage systems, facilitating adoption of the system and method. Further, the monitoring of pleural gases may provide an opportunity to investigate and modulate the pleural gas mixture to promote lung healing. For example, according to certain embodiments, supplemental oxygen may be administered (and potentially suction modulated) to vary the composition of the gas mixture within the chest cavity, potentially facilitating healing. This also may have an effect in reducing hospital stay and associated costs.

The following examples provide a comparison of the gas analysis techniques according to the present disclosure with the conventional visual inspection techniques. In addition, the examples provide a comparison of the duration of hospital stay for patients with chest tubes who receive supplemental oxygen and, in some cases, modulated suction to the duration of hospital stay for patients that receive standard chest tube care.

Example 1

Conventional visual inspection techniques and the gas analysis techniques according to embodiments of the present disclosure were compared in fifty patients undergoing lobectomy.

The mean age of the study cohort was 53.1±11.0 years, while the Male:Female ratio was 29:21. Patients had postresection predicted FEV1 and DLCO>40%. Thirty patients (60%) had a right-sided lobectomy, while 20 patients (40%) had left-sided lobectomy, 29 patients (58%) had upper lobectomies, 19 patients (38%) had lower lobectomies, and 2 patients (4%) had middle lobectomies.

All patients had a single 24 or 28 F chest tube placed intraoperatively. The chest tubes were kept on suction at −20 cm after surgery, and switched to water seal drainage on post-operative day 1.

When the staff surgeon deemed that the fluid output had reached the removal threshold, the comparison between visual inspection and gas analysis was performed. Stated slightly differently, Day 0 represents the start of serial analysis when the fluid output decreased to below removal threshold for the surgeon. The mean duration for the fluid output to fall below the individual surgeon's threshold from the day of surgery was 1.8±0.7 days.

Visual Inspection

For analysis of air leak by visual inspection, the patient was asked to cough five times and then take five deep breaths. This sequence was repeated twice. The first sequence was directed towards eliminating any trapped air in the pleural space or the tubing. Visual inspection was considered positive if air bubbles were detected during the second sequence.

Gas Analysis

Gas analysis was performed at the sampling port of the chest draining system. The sampling tubing was first connected to the chest drainage system and $CO_2$ and $O_2$ recorded. Supplemental $O_2$ was then administered nasally. Patients were allowed to take deep breaths for one minute, after which the values of $CO_2$ and $O_2$ were recorded.

A pleural $CO_2<1\%$ and/or an increase in $O_2<2\%$ with the administration of supplemental $O_2$ of 5 liters/min was determined to indicated the absence of a true leak. Additionally, a pleural $CO_2>1\%$ with an increase in $O_2 \geq 2\%$ with the administration of supplemental $O_2$ of 5 liters/min was determined to indicate a true leak. As to a pleural $CO_2>1\%$ with an increase in $O_2<2\%$ with the administration of supplemental $O_2$ of 5 liters/min, this was determined to suggest a recently resolved air leak (i.e., no true air leak).

End Points

Patients were followed for development of pneumothorax for three weeks after surgery. The primary end points were development of pneumothorax following chest tube removal on a chest radiograph obtained within four hours, readmissions for pneumothorax, and evidence of pneumothorax on the chest radiograph obtained at the post-operative visit at 2-3 weeks.

Statistical Analysis

Statistical analysis was performed using Microsoft Excel 2011 (Microsoft Corp, Redmond, Wash.) and GraphPad Prism, version 6 (GraphPad Software Inc, San Diego, Calif.). Two-tailed student and Fisher exact t-tests were used as appropriate. Statistical significance was defined at $p<0.05$.

Discussion of Results

Visual inspection revealed bubbles as to 31 patients, suggesting air leaks in those patients. By contrast, gas analysis indicated an air leak in only 19 patients. The comparison of the results suggested that the visual inspection techniques provided 12 false indications of an air leak.

To confirm that visual inspection was providing a false indication of an air leak, the chest tubes were clamped for 8 of the 12 patients in the group for which gas analysis suggested there was no air leak. A subsequent chest radiograph of those patients taken after four hours was normal, and the tubes were removed completely without development of pneumothorax. This led to the conclusion that the visual inspection determinations that an air leak was present were in fact false. As to the remaining 4 patients, no clamp trial was performed, and instead the chest tubes were removed directly. None of the 12 patients developed pneumothorax during three weeks of post-operative follow-up.

In addition, the 19 patients for which both visual inspection and gas analysis suggested air leaks were serially monitored to determine any discrepancy between the two techniques. The chest tubes were removed only if visual inspection was negative for air leak. As seen in Table 1, a greater proportion of patients tested positive for air leak by visual inspection than by gas analysis every day. As demonstrated above, a positive visual inspection but negative gas analysis suggests a false determination of an air leak by visual inspection. Therefore, it is believed that visual inspection over-estimates the prevalence of air leaks on each post-operative day.

TABLE 1

| | Day 0 | Day 1 | Day 2 | Day 3 | Day 4 | Day 5 |
|---|---|---|---|---|---|---|
| Visual Inspection indicates air leak | 19 (100%) | 14 (74%) | 12 (63%) | 7 (37%) | 4 (16%) | 3 (11%) |
| Gas Analysis indicates air leak | 19 (100%) | 10 (53%) | 5 (26%) | 4 (21%) | 2 (10%) | 2 (10%) |

Visual inspection also revealed no bubbles as to 19 patients, suggesting no air leaks in those patients. By contrast, gas analysis suggested that 2 of 19 patients actually did have an air leak. The comparison of the results suggested that the visual inspection techniques provided 2 false indications of no air leak.

To confirm that visual inspection was providing a false indication of no air leak, the chest tubes were removed from both the patients for whom gas analysis suggested there was an air leak. A radiograph taken within two hours indicated the development of a large pneumothorax in both patients. As a consequence, visual inspection might not be sensitive to detect small air leaks that do not cause bubbles, but can still lead to pneumothorax.

On the other hand, there was concordance between visual inspection and gas analysis as to 36 of the 51 patients. In fact, in 17 patients there was no air leak detected by both visual inspection and gas analysis. One of these patients, however, developed pneumothorax following tube removal.

In conclusion, of the 50 patients involved in the experiment, 22 patients had air leaks (19 of which were determined using both techniques, 2 of which were determined using only the gas analysis technique, and 1 of which was not determined by either technique). Stated slightly differently, the visual inspection technique failed to identify air leaks in 3 patients and identified air leaks in 12 patients where no air leak existed. By contrast, the gas analysis technique accurately demonstrated air leaks in 21 with only 1 false negative and no false positives. Accordingly, the gas analysis technique demonstrated better sensitivity (95.5% vs 86.4%), specificity (100% vs 57.1%), positive predictive value (100% vs 61.3%), and negative predictive value (96.6% vs 84.2%) in detection of air leaks.

Example 2

Conventional visual inspection techniques and the gas analysis techniques according to embodiments of the present disclosure were compared in 240 patients who either had undergone a procedure or were receiving treatment for a condition that required a chest tube.

The trial included 120 patients having had lung resections, 50 patients with spontaneous pneumothorax, 30 patients having had cardiac surgery, 15 patients having had a decortication, 10 patients with iatrogenic pneumothorax, 5 patients with ARDS/barotrauma pneumothorax, and 10 patients with pleural effusion/pleurodiesis.

The standards for visual inspection, gas analysis, end points, statistical analysis are as above relative to Example 1.

Discussion of Results

Visual inspection revealed bubbles as to 130 patients, suggesting air leaks in those patients. By contrast, gas analysis indicated an air leak in only 101 patients. The comparison of the results suggested that the visual inspection techniques provided 29 false indications of an air leak.

To confirm that visual inspection was providing a false indication of an air leak, the chest tubes were removed in all 29 patients. None of the 29 patients developed pneumothorax. This led to the conclusion that the visual inspection determinations that an air leak was present were in fact false.

Visual inspection also revealed no bubbles as to 110 patients, suggesting no air leaks in those patients. By contrast, gas analysis suggested that 7 of 110 patients actually did have an air leak. The comparison of the results suggested that the visual inspection techniques provided 7 false indications of no air leak.

To confirm that visual inspection was providing a false indication of no air leak, the chest tubes were removed from 2 patients for whom gas analysis suggested there was an air leak. As to both patients, it was necessary to replace the chest tube after it was removed. As a consequence, visual inspection might not be sensitive to detect small air leaks that do not cause bubbles, but can still lead to pneumothorax.

In conclusion, of the 240 patients involved in the experiment, 108 patients had air leaks (101 of which were determined using both techniques, 7 of which were determined using only the gas analysis technique) and 132 patients had no air leaks (103 of which were determined using both techniques, 29 of which were determined using only the gas analysis technique). Stated slightly differently, the visual inspection technique failed to identify air leaks in 7 patients and identified air leaks in 29 patients where no air leak existed.

Example 3

The promotion of lung healing with the administration of supplemental $O_2$ and, in some cases, modulated suction was studied in regard to 20 patients with intrapleural (IP) $CO_2$ in excess of 5%. These 20 patients were alternatively assigned (i) to undergo intervention directed towards reducing the intrapleural $CO_2$ levels to less than 5% and increasing intrapleural $O_2$ levels to greater than 21% or (ii) managed according to standard practice (i.e., water seal drainage and weaned off of $O_2$). The data for the group that received intervention is presented in Table 2, below, and the data for the group that was managed according to the standard practice is presented in Table 3, below.

TABLE 2

| Patient - Int. | Size of Leak (chambers) | Initial IP CO2 level (%) | Initial IP O2 level (%) | Chest Drainage (cm H2O) | Suppl. O2 (1/min) | Post-Int. CO2 level (%) | Post-Int. O2 level (%) | Duration of Leak (days) |
|---|---|---|---|---|---|---|---|---|
| 1 | 2 | 6.2 | 16 | −20 | 2 | 4.9 | 25 | 2 |
| 2 | 1 | 6.4 | 17 | −20 | 4 | 4.8 | 25 | 2 |
| 3 | 1 | 7.1 | 18 | −20 | 4 | 4.1 | 24 | 3 |
| 4 | 2 | 6.1 | 15 | −30 | 2 | 4.5 | 26 | 2 |
| 5 | 4 | 8.1 | 11 | −40 | 3 | 3 | 32 | 3 |
| 6 | 3 | 6.6 | 14 | −20 | 4 | 2.9 | 25 | 3 |
| 7 | 2 | 6 | 15 | −20 | 4 | 3.9 | 29 | 3 |
| 8 | 2 | 6.9 | 16 | −20 | 2 | 4.4 | 33 | 2 |
| 9 | 2 | 6.8 | 17 | −20 | 3 | 4.5 | 28 | 2 |
| 10 | 3 | 5.9 | 15 | −20 | 4 | 4.1 | 24 | 2 |
| Mean ± STDev | 2.2 ± 0.9 | 6.6 ± 1.2 | 15.4 ± 1.9 | | | 4.1 ± 0.7 | 27.1 ± 3.3 | 2.4 ± 0.5 |

TABLE 3

| Patient - Standard Practice | Size of Leak (chambers) | Initial IP $CO_2$ level (%) | Initial IP $O_2$ level (%) | Duration of Leak (days) |
|---|---|---|---|---|
| 1 | 1 | 6.1 | 18 | 5 |
| 2 | 2 | 6.8 | 15 | 6 |
| 3 | 2 | 6.1 | 16 | 7 |
| 4 | 2 | 7.1 | 17 | 5 |
| 5 | 1 | 6.8 | 14 | 8 |
| 6 | 1 | 6.2 | 13 | 6 |
| 7 | 2 | 6.6 | 16 | 4 |
| 8 | 4 | 8.1 | 14 | 6 |
| 9 | 3 | 8.2 | 15 | 6 |
| 10 | 2 | 6.2 | 13 | 7 |
| Mean ± STDev | 2.0 ± 0.9 | 6.8 ± 0.9 | 15.1 ± 1.7 | 6 ± 1.2 |

There was no difference in the size of air leak between the two groups (intervention group 2.2±0.9 chambers vs. standard practice 2.0±0.9 chambers). In addition, there was no difference between the two groups with regard to initial intrapleural $CO_2$ levels (intervention 6.6±1.2% vs. standard practice 6.8±0.9%). Further, there was no difference between the two groups with regard to initial intrapleural $O_2$ levels (intervention 15.4%±1.9% vs. standard practice 15.1%±1.7%).

The interventions to reduce the $CO_2$ levels included extrapleural suction up to −40 cm $H_2O$ and supplemental oxygen up to 4 l/min. The goal was to administer extrapleural suction and supplemental $O_2$ to achieve an intrapleural $CO_2$ level less than 5% and an intrapleural $O_2$ level greater than 21%. As seen in Table 2, the described intervention led to a reduction in intrapleural $CO_2$ levels from 6.6%±1.2% to 4.1%±0.7% and increase in $O_2$ from 15.4%±1.9% to 27.1%±3.3%. Comparing Table 2 to Table 3, it will be recognized that the patients that underwent intervention showed significantly decreased duration of air leaks compared to those that did not (intervention 2.4±0.5 days vs. standard practice 6.0±1.2 days).

Although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

Figure 7:
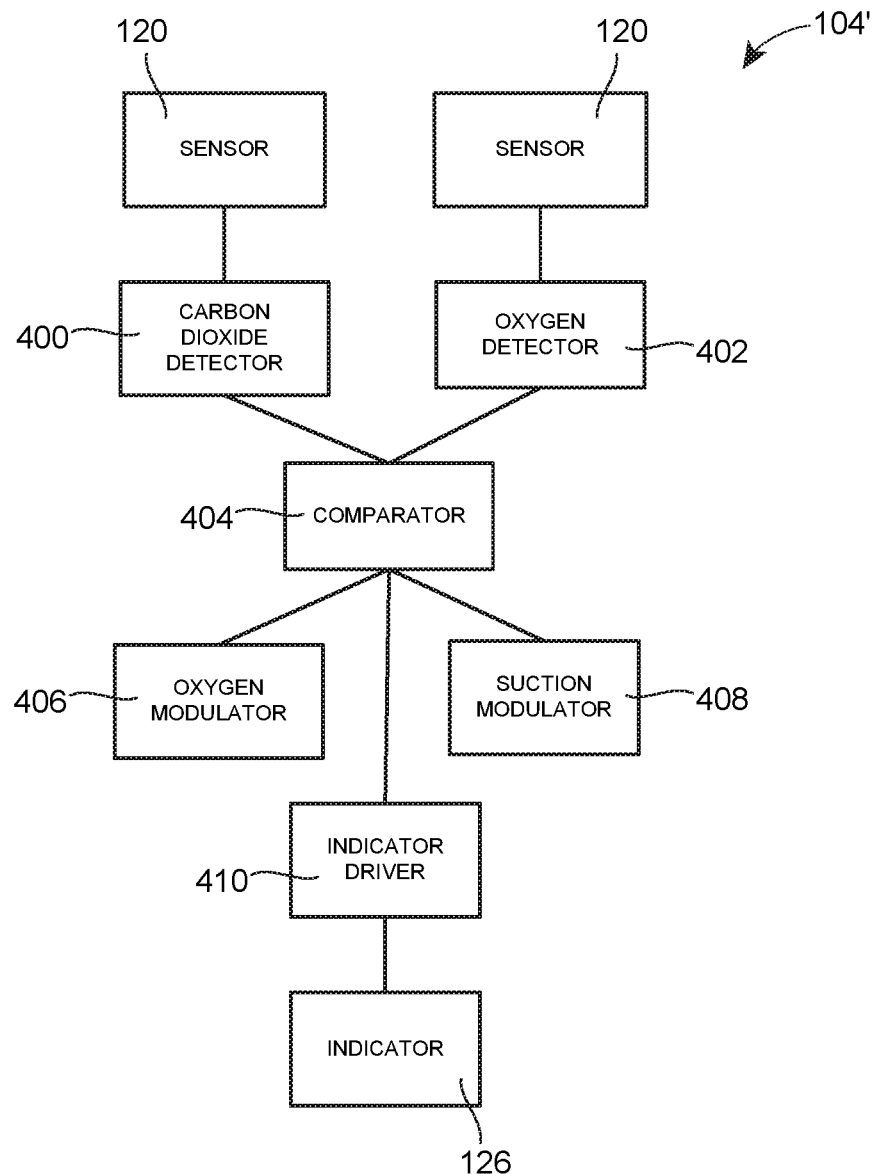
FIG. 7 is a schematic view of an alternative embodiment of an analyzer.

As one example of an alternative embodiment, FIG. 7 includes a block diagram of an analyzer 104'. The analyzer 104' includes a carbon dioxide detector 400, an oxygen detector 402, a comparator 404, an oxygen modulator 406, a suction modulator 408, and an indicator driver 410. As described above, each of the detectors 400, 402, the comparator 404, each of the modulators 406, 408, and the indicator driver 410 may be defined by individual circuits, or a microprocessor or other programmable device with associated firmware or software. In fact, all of the elements of the analyzer 104' may be defined by a processor and associated memory, which memory may be used to store instructions that cause the processor to carry out the actions of the individual elements.

According to this embodiment, the carbon dioxide detector 400 and the oxygen detector 402 are coupled to sensors 120 that determine the level of carbon dioxide, oxygen, or both. Each of the detectors 400, 402 receive signals from the sensors 120 and provide an output to the comparator 404, which element determines whether the level of carbon dioxide and/or oxygen exceeds the thresholds set for those levels, as discussed above. Furthermore, the oxygen modulator 406 is coupleable to an oxygen source, and may modify the administration of the oxygen to the patient (i) as part of the process of determining the level of oxygen in the intrapleural space and/or (ii) as part of the process of modifying or altering the level of oxygen in the intrapleural space to change the level of oxygen in the intrapleural space. In a similar fashion, the suction modulator 408 may alter the level of suction applied via the drainage system 102 to modify or alter the level of carbon dioxide in the intrapleural space.

The modulators 406, 408 may be coupled to the comparator 404 to receive a signal or other output therefrom to control the rate at which the modulators 406, 408 control the associated oxygen supply or suction to modify or alter the gaseous milieu in the intrapleural space. The indicator driver 410 also may be coupled to the comparator 404, and may receive a signal or other output therefrom to control the indicator 126 no that the surgeon or other healthcare professional may be able to determine whether to remove the chest tube.

Other examples of alternative embodiments are discussed in the following numbered paragraphs. Moreover, while discussed in terms of a system including both drainage system and analyzer, the present disclosure also encompasses the analyzer separate from the drainage system to which it may be coupled.

1. A system comprising:
a chest tube drainage system comprising a first chamber in fluid communication with a port connectable to a chest tube, a second chamber in fluid communication with a port connectable to a suction device, and a fluid seal connected to and disposed between the first chamber and the second chamber;
one or more gas sensors attached to the chest tube drainage system, the one or more gas sensors configured to detect at least one of gaseous carbon dioxide and gaseous oxygen;
a controller connected to the one or more gas sensors; and
at least one indicator coupled to the controller,
the controller configured to determine if a threshold level of carbon dioxide is exceeded, and to activate the at least one indicator if the threshold level of carbon dioxide is not exceeded.

2. The system according to paragraph 1, wherein the threshold level of carbon dioxide is 1%.

3. The system according to paragraph 1, wherein the controller is configured to determine if a threshold level of oxygen is exceeded if the threshold level of carbon dioxide is exceeded, and to activate the at least one indicator if the threshold level of oxygen is not exceeded.

4. The system according to paragraph 3, wherein the threshold level of oxygen is 1%.

5. The system according to paragraph 3, wherein the threshold level of oxygen is 2%.

6. The system according to paragraph 3, further comprising a clamp disposed between the port connectable to a chest tube and the chest tube, and a pressure sensor disposed between the clamp and the chest tube and connected to the controller, wherein the controller configured to determine if a threshold pressure is exceeded at the pressure sensor if the threshold level of oxygen is exceeded, and to activate the at least one indicator if the threshold pressure is not exceeded.

7. The system according to paragraph 6, wherein the threshold level of oxygen is less than 5%.

8. The system according to paragraph 1, further comprising an oxygen source coupled to the controller, the controller configured to activate the oxygen source if the threshold level of carbon dioxide is exceeded.

9. The system according to paragraph 8, wherein controller is configured to determine if a threshold level of oxygen is exceeded after the oxygen source is activated, and to activate the at least one indicator if the threshold level of oxygen is not exceeded.

10. The system according to paragraph 9, wherein the controller is configured to activate the oxygen source if the threshold level of carbon dioxide is exceeded and a second threshold level of carbon dioxide is not exceeded, and to determine if a threshold level of oxygen is exceeded after the oxygen source is activated, and to activate the at least one indicator if the threshold level of oxygen is not exceeded.

11. The system according to paragraph 10, wherein the threshold level of oxygen is 1%.

12. The system according to paragraph 10, wherein the threshold level of oxygen is 2%.

13. The system according to paragraph 10, further comprising a clamp disposed between the port connectable to a chest tube and the chest tube, and a pressure sensor disposed between the clamp and the chest tube and connected to the controller, wherein the controller configured to determine if a threshold pressure is exceeded at the pressure sensor if the threshold level of oxygen is exceeded, and to activate the at least one indicator if the threshold pressure is not exceeded.

14. The system according to paragraph 10, wherein the controller is configured to activate the oxygen source if the threshold level of carbon dioxide is exceeded and the second threshold level of carbon dioxide is exceeded to increase the level of oxygen above an intervention level.

15. The system according to paragraph 14, wherein the controller is configured to modulate suction to the drainage system if the second threshold level of carbon dioxide is exceeded to decrease the level of carbon dioxide below an intervention level.

16. A system comprising:
a chest tube drainage system comprising a first chamber in fluid communication with a port connectable to a chest tube, a second chamber in fluid communication with a port connectable to a suction device, and one-way valve connected to and disposed between the first chamber and the second chamber;
one or more gas sensors attached to the chest tube drainage system, the one or more gas sensors configured to detect at least one of gaseous carbon dioxide and gaseous oxygen;
a controller connected to the one or more gas sensors; and
at least one indicator coupled to the controller,
the controller configured to determine if a threshold level of carbon dioxide is exceeded, and to activate the at least one indicator if the threshold level of carbon dioxide is not exceeded.

17. The system according to paragraph 16, wherein the threshold level of carbon dioxide is 1%.

18. The system according to paragraph 16, wherein the controller is configured to determine if a threshold level of oxygen is exceeded if the threshold level of carbon dioxide is exceeded, and to activate the at least one indicator if the threshold level of oxygen is not exceeded.

19. The system according to paragraph 18, wherein the threshold level of oxygen is 1%.

20. The system according to paragraph 18, wherein the threshold level of oxygen is 2%.

21. The system according to paragraph 18, further comprising a clamp disposed between the port connectable to a chest tube and the chest tube, and a pressure sensor disposed between the clamp and the chest tube and connected to the controller, wherein the controller configured to determine if a threshold pressure is exceeded at the pressure sensor if the threshold level of oxygen is exceeded, and to activate the at least one indicator if the threshold pressure is not exceeded.

22. The system according to paragraph 21, wherein the threshold level of oxygen is less than 5%.

23. The system according to paragraph 16, further comprising an oxygen source coupled to the controller, the controller configured to activate the oxygen source if the threshold level of carbon dioxide is exceeded.

24. The system according to paragraph 23, wherein controller is configured to determine if a threshold level of oxygen is exceeded after the oxygen source is activated, and to activate the at least one indicator if the threshold level of oxygen is not exceeded.

25. The system according to paragraph 24, wherein the controller is configured to activate the oxygen source if the threshold level of carbon dioxide is exceeded and a second threshold level of carbon dioxide is not exceeded, and to determine if a threshold level of oxygen is exceeded after the oxygen source is activated, and to activate the at least one indicator if the threshold level of oxygen is not exceeded.

26. The system according to paragraph 25, wherein the threshold level of oxygen is 1%.

27. The system according to paragraph 25, wherein the threshold level of oxygen is 2%.

28. The system according to paragraph 25, further comprising a clamp disposed between the port connectable to a chest tube and the chest tube, and a pressure sensor disposed between the clamp and the chest tube and connected to the controller, wherein the controller configured to determine if a threshold pressure is exceeded at the pressure sensor if the threshold level of oxygen is exceeded, and to activate the at least one indicator if the threshold pressure is not exceeded.

29. The system according to paragraph 25, wherein the controller is configured to activate the oxygen source if the threshold level of carbon dioxide is exceeded and the second threshold level of carbon dioxide is exceeded to increase the level of oxygen above an intervention level.

30. The system according to paragraph 29, wherein the controller is configured to modulate suction to the drainage system if the second threshold level of carbon dioxide is exceeded to decrease the level of carbon dioxide below an intervention level.

31. A system comprising:
a chest tube drainage system comprising a first chamber in fluid communication with a port connectable to a chest tube, a second chamber in fluid communication with a port connectable to a suction device, and a one-way valve connected to and disposed between the first chamber and the second chamber;
one or more gas sensors attached to the chest tube drainage system, the one or more gas sensors configured to detect gaseous carbon dioxide;
a controller connected to the one or more gas sensors; and
at least one indicator coupled to the controller,
the controller configured to determine if a threshold level of carbon dioxide is exceeded, and to activate the at least one indicator if the threshold level of carbon dioxide is not exceeded to signal that the chest tube may be removed.

32. A system comprising:

a chest tube drainage system comprising a first chamber in fluid communication with a port connectable to a chest tube, a second chamber in fluid communication with a port connectable to a suction device, and a one-way valve connected to and disposed between the first chamber and the second chamber;

one or more gas sensors attached to the chest tube drainage system, one of the one or more gas sensors configured to detect gaseous carbon dioxide and one of the one or more gas sensors configured to detect gaseous oxygen;

a controller connected to the one or more gas sensors; and at least one indicator coupled to the controller, the controller configured (a) to determine if a threshold level of carbon dioxide is exceeded, and to activate the at least one indicator if the threshold level of carbon dioxide is not exceeded to signal that the chest tube may be removed, and (b) to determine if a threshold level of oxygen is exceeded if the threshold level of carbon dioxide is exceeded, and to activate the at least one indicator if the threshold level of oxygen is not exceeded to signal that the chest tube may be removed.

33. A system comprising:

a chest tube drainage system comprising a first chamber in fluid communication with a port connectable to a chest tube, a second chamber in fluid communication with a port connectable to a suction device, and a one-way valve connected to and disposed between the first chamber and the second chamber;

one or more gas sensors attached to the chest tube drainage system, the one or more gas sensors configured to detect gaseous carbon dioxide;

a clamp disposed between the port connectable to a chest tube and the chest tube, and a pressure sensor disposed between the clamp and the chest tube and connected to the controller, a controller connected to the one or more gas sensors; and at least one indicator coupled to the controller, the controller configured (a) to determine if a threshold level of carbon dioxide is exceeded, and to activate the at least one indicator if the threshold level of carbon dioxide is not exceeded to signal that the chest tube may be removed, (b) to determine if a threshold level of oxygen is exceeded if the threshold level of carbon dioxide is exceeded, and to activate the at least one indicator if the threshold level of oxygen is not exceeded to signal that the chest tube may be removed, and (c) to determine if a threshold pressure is exceeded at the pressure sensor if the threshold level of oxygen is exceeded, and to activate the at least one indicator if the threshold pressure is not exceeded to signal that the chest tube may be removed.

34. A system comprising:

a chest tube drainage system comprising a first chamber in fluid communication with a port connectable to a chest tube, a second chamber in fluid communication with a port connectable to a suction device, and a one-way valve connected to and disposed between the first chamber and the second chamber;

one or more gas sensors attached to the chest tube drainage system, the one or more gas sensors configured to detect gaseous carbon dioxide;

at least one indicator;

an oxygen source;

a controller connected to the one or more gas sensors, the at least one indicator, and the oxygen source, the controller configured (a) to determine if a threshold level of carbon dioxide is exceeded, and to activate the at least one indicator if the threshold level of carbon dioxide is not exceeded to signal that the chest tube may be removed, and (b) to activate the oxygen source if the threshold level of carbon dioxide is exceeded.

35. The system according to paragraph 34, further comprising a clamp disposed between the port connectable to a chest tube and the chest tube, and a pressure sensor disposed between the clamp and the chest tube and connected to the controller, wherein the controller configured to determine if a threshold pressure is exceeded at the pressure sensor if a threshold level of oxygen is exceeded, and to activate the at least one indicator if the threshold pressure is not exceeded.

36. A method of determining if a chest tube is to be removed, the method comprising the steps of:

determining if a threshold level of carbon dioxide is exceeded in a chest tube drainage system connected to a chest tube downstream of a liquid seal; and removing the chest tube if the threshold level of carbon dioxide is not exceeded.

37. The method according to paragraph 36, further comprising: administering supplemental oxygen if the carbon dioxide level is exceeded.

38. The method according to paragraph 36, further comprising: applying additional suction through the chest tube if the carbon dioxide level is exceeded.

39. The method according to paragraph 36, further comprising: determining if a threshold level of oxygen is exceeded in the chest tube drainage system; and removing the chest tube if the threshold level oxygen is not exceeded.

40. The method according to paragraph 36, further comprising: administering supplemental oxygen if the threshold level of carbon dioxide is not exceeded; determining if a threshold level of oxygen is exceeded in the chest tube drainage system after administering supplemental oxygen; and removing the chest tube if the threshold level oxygen is not exceeded.

41. The method according to paragraph 40, further comprising: disposing a clamp between the chest tube and the chest tube drainage system; determining if a threshold pressure is exceeded downstream of the clamp; and removing the chest tube if the threshold pressure is not exceeded.

42. The method according to paragraph 39, further comprising: administering additional supplemental oxygen if the oxygen level is exceeded.

43. The method according to paragraph 39, further comprising: applying additional suction through the chest tube if the oxygen level is exceeded.

44. A system comprising:

a chest tube drainage system comprising a first chamber in fluid communication with a port connectable to a chest tube, a second chamber in fluid communication with a port connectable to a suction device, and a fluid seal connected to and disposed between the first chamber and the second chamber; and one or more gas sensors disposed at the port connectable to the suction device or between the port and the fluid seal, the one or more gas sensors configured to detect at least one of gaseous carbon dioxide and gaseous oxygen.

45. The system according to paragraph 44, wherein the one or more gas sensors are disposed at the port connectable to the suction device.

46. The system according to paragraph 44, further comprising a clamp disposed between the port connectable to a chest tube and the chest tube, and a pressure sensor disposed between the clamp and the chest tube.

47. The system according to paragraph 44, further comprising a controller connected to the one or more gas sensors and at least one indicator coupled to the controller, wherein the controller configured to determine if a threshold level of carbon dioxide is exceeded, and to activate the at least one indicator if the threshold level of carbon dioxide is not exceeded.

48. The system according to paragraph 47, wherein the controller configured to determine if a threshold level of oxygen is exceeded if the threshold level of carbon dioxide is exceeded, and to activate the at least one indicator if the threshold level of oxygen is not exceeded.

49. The system according to paragraph 48, further comprising a clamp disposed between the port connectable to a chest tube and the chest tube, and a pressure sensor disposed between the clamp and the chest tube and connected to the controller, wherein the controller configured to determine if a threshold pressure is exceeded at the pressure sensor if the threshold level of oxygen is exceeded, and to activate the at least one indicator if the threshold pressure is not exceeded.

It should also be understood that, unless a term is expressly defined in this patent using the sentence "As used herein, the term ' . . . ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

What is claimed is:

1. A method of determining if it is proper for a chest tube to be removed, the method comprising the steps of:
   detecting a gas at a point downstream of a liquid seal in a chest tube drainage system connected to the chest tube, the gas having leaked from a lung into the pleural space, the gas selected from the group consisting of gaseous carbon dioxide and gaseous oxygen;
   determining if an upper threshold level of carbon dioxide is exceeded at the point downstream of the liquid seal; and
   removing the chest tube if the upper threshold level of carbon dioxide is not exceeded.

2. The method according to claim 1, further comprising:
   administering supplemental oxygen if the upper threshold level of carbon dioxide is exceeded.

3. The method according to claim 1, further comprising:
   applying suction of higher intensity through the chest tube if the upper threshold level of carbon dioxide is exceeded.

4. The method according to claim 1, further comprising:
   determining if a threshold level of oxygen is exceeded in the chest tube drainage system; and
   removing the chest tube if the threshold level of oxygen is not exceeded.

5. The method according to claim 4, further comprising:
   administering additional supplemental oxygen if the threshold level of oxygen is exceeded.

6. The method according to claim 4, further comprising:
   applying suction of higher intensity through the chest tube if the threshold level of oxygen is exceeded.

7. The method according to claim 1, further comprising:
   administering supplemental oxygen if the threshold level of carbon dioxide is not exceeded;
   determining if a threshold level of oxygen is exceeded in the chest tube drainage system after administering supplemental oxygen; and
   removing the chest tube if the threshold level of oxygen is not exceeded.

8. The method according to claim 7, further comprising:
   disposing a clamp between the chest tube and the chest tube drainage system;
   determining if a threshold pressure is exceeded between the clamp and a patient's chest cavity; and
   removing the chest tube if the threshold pressure is not exceeded.

* * * * *